US008847175B2

(12) United States Patent
Laidevant et al.

(10) Patent No.: US 8,847,175 B2
(45) Date of Patent: Sep. 30, 2014

(54) METHOD FOR LOCATING AN OPTICAL MARKER IN A DIFFUSING MEDIUM (75) Inventors: Aurélie Laidevant, Rumilly (FR); Jean-Marc Dinten, Lyons (FR); Anne-Sophie Montcuquet, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 216 days.

(21) Appl. No.: 13/325,444

(22) Filed: Dec. 14, 2011

(65) Prior Publication Data

US 2012/0153187 A1 Jun. 21, 2012

(30) Foreign Application Priority Data

Dec. 15, 2010 (FR) ...................................... 10 60567

(51) Int. Cl.
    *G01N 21/64* (2006.01)
    *G01N 21/49* (2006.01)
    *A61B 5/00* (2006.01)

(52) U.S. Cl.
    CPC .......... *A61B 5/0073* (2013.01); *G01N 21/6408* (2013.01); *G01N 2021/6484* (2013.01); *G01N 21/49* (2013.01); *G01N 21/6456* (2013.01); *G01N 21/6428* (2013.01)
    USPC ..................... 250/458.1; 250/459.1

(58) Field of Classification Search
    CPC .................................................. G01N 21/6408
    USPC ........................................... 250/458.1, 459.1
    See application file for complete search history.

(56) References Cited

U.S. PATENT DOCUMENTS 6,138,046 A    10/2000   Dalton
6,304,771 B1   10/2001   Yodh et al.
(Continued)

FOREIGN PATENT DOCUMENTS

EP          1884765 A1    2/2008
EP      2 063 257 A2    5/2009
(Continued)

OTHER PUBLICATIONS

A. Laidevant, et al., "Analytical method for localizing a fluorescent inclusion in a turbid medium", Applied Optics, Apr. 10, 2007, vol. 46, No. 11, pp. 2131-2137.

(Continued)

*Primary Examiner* — Constantine Hannaher
(74) *Attorney, Agent, or Firm* — Oblon, Spivak, McClelland, Maier & Neustadt, L.L.P.

(57) ABSTRACT

A method for locating at least one optical marker in a diffusing medium, the marker having at least one optical property different from the diffusing medium, wherein: a) a pulsed radiation interacts with the medium and the at least one optical marker, producing an optical signal, and at least one acquisition of data of the optical signal is performed, each acquisition including one or more time components of interest, due to the at least one marker, and a spurious component, due to the medium other than the at least one marker, b) a multidimensional array X is formed from the optical signal data of the at least one of the acquisitions, c) the array X is processed by factorization into a product of only two non-negative multidimensional arrays A and S, and d) at least one of the time components is extracted from the arrays A and S.

20 Claims, 7 Drawing Sheets (56) References Cited

U.S. PATENT DOCUMENTS

| | | | |
|---|---|---|---|
| 6,825,930 | B2 | 11/2004 | Cronin et al. |
| 7,321,791 | B2 | 1/2008 | Levenson et al. |
| 7,477,931 | B2 | 1/2009 | Hoyt |
| 7,508,505 | B2 * | 3/2009 | Lustenberger et al. ........ 356/317 |
| 7,672,834 | B2 | 3/2010 | Smaragdis |
| 7,675,044 | B2 | 3/2010 | Laidevant et al. |
| 2002/0072677 | A1 | 6/2002 | Sevick-Muraca et al. |
| 2005/0040769 | A1 | 2/2005 | Enz |
| 2005/0065440 | A1 | 3/2005 | Levenson |
| 2005/0264805 | A1 | 12/2005 | Cromwell et al. |
| 2006/0135769 | A1 | 6/2006 | Angibaud et al. |
| 2006/0149479 | A1 | 7/2006 | Ma |
| 2008/0051665 | A1 | 2/2008 | Xu et al. |
| 2008/0103390 | A1 | 5/2008 | Contag et al. |
| 2008/0200780 | A1 | 8/2008 | Schenkman et al. |
| 2009/0024561 | A1 | 1/2009 | Palanisamy |
| 2009/0046291 | A1 | 2/2009 | VanDer Mark et al. |
| 2009/0065710 | A1 | 3/2009 | Hunziker et al. |
| 2009/0141959 | A1 | 6/2009 | Can et al. |
| 2009/0153850 | A1 | 6/2009 | Nielsen et al. |
| 2009/0245605 | A1 | 10/2009 | Levenson et al. |
| 2009/0245611 | A1 | 10/2009 | Can et al. |
| 2011/0068280 | A1 | 3/2011 | Herve et al. |
| 2012/0032094 | A1 * | 2/2012 | Montcuquet et al. ...... 250/459.1 |

FOREIGN PATENT DOCUMENTS

| | | | |
|---|---|---|---|
| EP | 2 302 362 A1 | 3/2011 | |
| GB | 2 231 958 A | 11/1990 | |
| JP | 2008-215881 | 9/2008 | |
| WO | WO 96/20638 | 7/1996 | |
| WO | WO 96/26431 | 8/1996 | |
| WO | WO 01/09605 A1 | 2/2001 | |
| WO | WO 01/50955 A1 | 7/2001 | |
| WO | WO 2005/043138 A1 | 5/2005 | |
| WO | WO 2006/032151 A1 | 3/2006 | |
| WO | WO 2006/062895 A2 | 6/2006 | |
| WO | WO 2006/087437 A3 | 8/2006 | |
| WO | WO 2006/135769 A1 | 12/2006 | |
| WO | WO 2008/132522 | 11/2008 | |
| WO | WO 2010103026 A1 * | 9/2010 | |

OTHER PUBLICATIONS

Jerome Boutet, et al., "Bimodal ultrasound and fluorescence approach for prostate cancer diagnosis", Journal of Biomedical Optics 14(6), 064001, Nov./Dec. 2009, pp. 064001-1-064001-7.

Fen Gao, et al., "Time-Domain Fluorescence Molecular Tomography Based on Generalized Pulse Spectrum Technique", Proceedings Biomed, 2006, 3 pages.

Stylianos Psycharakis, et al., "Autofluorescence removal from fluorescence tomography data using multispectral imaging" SPIE-OSA/ vol. 6626, 2007, pp. 662601-1-662601-7.

Anand T. N. Kumar, et al., "Fluorescence-lifetime-based tomography for turbid media", Optics Letters, Dec. 15, 2005, vol. 30, No. 24 , pp. 3347-3349.

Anand T. N. Kumar, et al., "Feasibility of in vivo imaging of fluorescent proteins using lifetime contrast", Optics Letters, vol. 34, No. 13, Jul. 1, 2009 pp. 2066-2068.

S. Lam, et al., "Time Domain Fluorescent Diffuse Optical Tomography: analytical expressions", Optics Express, Apr. 4, 2005 ,vol. 13, No. 7, pp. 2263-2275.

Daniel D. Lee, et al., "Learning the parts of objects by non-negative matrix factorization", Letters to Nature, Nature, vol. 401, Oct. 21, 1999, pp. 788-791.

James R. Mansfield, et al., "Autofluorescence removal, multiplexing, and automated analysis methods for in-vivo fluorescence imaging", Journal of Biomedical Optics, 10(4), Jul./Aug. 2005, 041207-1-041207-9.

Tamara Troy, et al., "Quantitative Comparison of the Sensitivity of Detection of Fluorescent and Bioluminescent Reporters in Animal Models", Molecular Imaging, vol. 3, No. 1, Jan. 2004, pp. 9-23, pp. 9-23.

Douglas Wood, et al., "Refining epifluorescence imaging and analysis with automated multiple-band flat-field correction", Nature Methods, Carestream Molecular Imaging, Apr. 2008, 2 pages (i-ii).

A. Chichocki, et al., "Multilayer nonnegative matrix factorization", Electronics Letter, XP6027125A, Aug. 3, 2006, vol. 42, No. 16, 2 pages.

Cyril Gobinet, "Application de techniques de séparation de sources á la spectroscopie Raman et á la spectroscopie de fluorescence", University De Reims Champagne Ardenne, Mar. 27, 2006, pp. 73-114 (with English-language equivalent.

Dan Kalman, "A Singularly Valuable Decomposition: The SVD of a Matrix", The College Mathematics Journal, vol. 27, No. 1, Jan. 1996, 22 pages.

G. W. Stewart, "On the Early History of the Singular Value Decomposition", SIAM Review, vol. 35, Issue 4, 1993, http://www.jstor.org, pp. 551-566.

Lionel Herve et al., "Localization of Fluorescence marked prostate tumor with time-resolved diffuse optical tomography," Multimodal Biomedical Imaging, Multimodal Biomedical Imaging, vol. 7557, pp. 1-9, (Feb. 23, 2010).

Anne-Sophie Mon6tcuquet et al., "Non-Negative Matrix Factorization: A Blind Sources Separation Method to Unmix Fluorescence Spectra," IEEE, (2009), <doi:10.1109/WHISPERS.2009.3289009>.

Julie Falconet et al., "Estimation of optical properties of turbid media: experimental comparison of spatially and temporally resolved reflectance methods,", Applied Optics, vol. 47. No. 11, pp. 1734-1739 (Apr. 10, 2008).

D.D. Lee and H.S. Seung, Algorithms for Non-negative Matrix Factorization, Advances Neural Information Processing Systems, 13, 556-562 (2001).

Aurelie Laidevant, Thesis, "Methodes optiques resolues en temps pour la tomographie de fluorescence dans les milieux diffusants," Joseph Fourier University, Grenoble, FR, Oct. 5, 2006 (with English Abstract).

D.G. Aggelis, et al., "Repair evaluation of concrete cracks using surface and through-transmission wave measurements," Cement & Concrete Composite 29, pp. 700-711 (2007), <doi:10.1016/j.cemconcomp.2007.05.001>.

Young-Fo Chang et al., "Time of flight diffraction imaging for double-probe technique," Ferroelectrics and Frequency Control, vol. 49, No. 6, p9. 1-15 (2002), <doi:10.1109/TUFF.2002.1009335>.

Young-Fo Chang et al. "A 3-D Image Detection Method of a Surface Opening Crack in Concrete Using Ultrasonic Transducer Arrays," Journal of Nondestructive Evaluation, vol. 16, No. 4, pp. 193-203 (1997).

J.C. Lagarias et al., "Convergence Properties of the Nelder-Mead Simplex Method in Low Dimensions," SIAM Journal on Optimization, vol. 9 (1), pp. 112-147 (1998), <doi:1137/S1052623496303470>.

* cited by examiner

METHOD FOR LOCATING AN OPTICAL MARKER IN A DIFFUSING MEDIUM

TECHNICAL FIELD AND PRIOR ART

This invention relates to the field of optical imaging, for example fluorescence imaging, in diffusing media and in particular the biological tissues. It implements time resolved optical methods.

It is applicable in the medical field, in particular in the fluorescence diffuse optical tomography for determining the distribution of fluorescent particles, for example markers.

The diffuse optical imaging, and in particular fluorescence imaging, offers the prospect of having non-invasive diagnostic systems thanks to the use of easy to use inexpensive non-ionizing radiations.

In applications implementing fluorescence imaging, fluorescent markers are injected in the subject and bind to some specific molecules, for example cancer tumours. The area of interest is lighted at the optimum excitation wavelength of the fluorophore (chemical substance of a molecule capable of emitting the fluorescence light after excitation) and the fluorescent signal is detected.

Then, from this fluorescent signal, obtaining localization or concentration information about the markers is attempted.

The fluorescence optical imaging (with an injection of the specific fluorophore) is currently limited to "small animal" applications due to the lack of markers adapted and injectable to human, and the tissue auto-fluorescence problem that arises for depth detection.

Indeed, to apply this cancer diagnostic method to humans, it is essential that the specific signal located deeper under the skin than in the small animal can be detected.

But the specific signal to be detected weakens with depth, mainly because of the tissue absorption and diffusion, and is confronted with a spurious signal which disturbs the detection. This signal, called "auto-fluorescence", described the fluorescence of tissues to which no specific chemical substance or fluorophore has been injected: this is the natural fluorescence of the tissue. When markers are located in depth (a few cm), their specific signal attenuates. Then, the auto-fluorescence can have not inconsiderable amplitude because it is emitted by the entire volume of biological tissues.

Furthermore, filtering the excitation light is not always perfect and a little excitation light can pass through the fluorescent filter intended to remove it and is added to the measured signal. Other elements of the measurement system (for example filters) can also have their own fluorescence which is low.

Both phenomena, auto-fluorescence peculiar to tissues and spurious signal due to the system, are phenomena which interfere and distort the fluorescence measurement.

The auto-fluorescence is a known phenomenon, but is to date rarely perceived as a spurious signal. In cancerology in particular, the auto-fluorescence is used to discriminate between cancer tissues and healthy tissues. The object is then not to inject the specific marker, but merely to observe the auto-fluorescence of specific areas and compare different areas of a same individual.

In contrast, the fluorescence optical spectroscopy generally uses red or near infrared excitation wavelengths, which ensure a lesser absorption of the signal into tissues, and thereby allow a better penetration of the tissues. The tissue auto-fluorescence is then much lower and becomes a signal to be removed rather than to be used.

In the following, the two effects which are the auto-fluorescence peculiar to tissues and the generation of spurious signal due to the system can be gathered under the term of spurious signal.

Different methods for subtracting images are known to restrict the auto-fluorescence effect in the case of an illumination of the medium by a continuous source.

According to one such method, a simple subtraction of the average signal of a region of the image which does not contain any fluorescent markers is carried out. A limitation of these techniques is the necessity to find a reference area without significant fluorescence and to reproduce similar acquisition conditions.

According to another type of method, a subtraction is performed using "background" filters shifted toward blue: this technique is carried out in the IVIS systems of Caliper Life Science. An image is taken with a filter shifted toward blue the role of which is to excite the auto-fluorescence, but not the fluorophores. This background image is then subtracted—to a nearest scale factor—from the regular image with the excitation filter. It is not sure that this fluorescence produced by a shifting toward blue is representative of the auto-fluorescence at the observation wavelength.

There are also methods based on spectral techniques, but of course they require to perform with wavelength resolved acquisitions.

Thus, a multispectral technique with excitations at different wavelengths has been described in US 2005065440.

Other works, see in particular those of D. Wood et al. "Refining epifluorescence imaging and analysis with automated multiple-band flat-field correction", published in Nature Methods Application Notes (2008), or S. Psycharakis et al., Autofluorescence removal from fluorescence tomography data using multispectral imaging (Proceedings Paper SPIE 662601-66260I-7 (2007)) also use a multispectral method based on a priori models of spectra. Some of those works have shown results in small animal tomography.

Finally, there are spectral decomposition methods (measurement at a single wavelength) to discriminate auto-fluorescence from fluorescence. A spectrometer enables the emission spectrum to be measured at each pixel of the image. The decomposition separates both spectra and enables two images to be obtained, one from auto-fluorescence, the other from fluorescence.

Some of these techniques carry out a separation of spectra by principal component analysis (PCA), other techniques by factorizing into non-negative matrices. Once again, the method is only applicable to continuous illuminations, that is not pulsed, factorizing into non negative matrices enabling the reconstruction of the wavelength spectrum of different components making up a detected fluorescence signal. By wavelength spectrum, it is meant an energy distribution (US 20090245611).

Other techniques implement an illumination of the medium by pulsed light, also called time resolved fluorescence. By pulsed light, it is meant a luminous pulse the duration of which is a few fs to a few ns. In this case, the detection of the signal emitted by the tissue is generally performed between two consecutive pulses of the luminous source.

Thus, in document A. T. Kumar et al. "Feasibility of in vivo imaging of fluorescent proteins using lifetime contrast", Optics Letters 34, 2066-2068 (2009), the fluorescence is discriminated from auto-fluorescence (AF) on a small animal by modelling the distribution of AF and the decay in fluorescence of the fluorophore. But this technique implements an a priori knowledge of the decay profiles to adjust the time measurements. This technique only enables a two dimension image to be carried out, but does not enable information on the depth localization of species of interest to be accessed.

Finally, in the technique described in the article of A. Laidevant et al. <<Analytical method for localizing a fluorescent inclusion in a turbid medium", Applied Optics, 46, 2131-2137 (2007), a specific measurement of the spurious signal is performed on the medium by removing the fluorescent inclusion. This measurement is then subtracted from the raw fluorescence signal. This technique is obviously time consuming (it requires to carry out a measurement without fluorescent inclusion and then a measurement with fluorescent inclusion) and is delicate to implement.

Generally, there is therefore the problem of finding a new method, not requiring implementing a spectral technique, that can be quickly performed (in view of in vivo application) and enabling the different contributions of luminous sources to be differentiated, and in particular the contributions of fluorescent sources and spurious sources, by resorting to a time resolved fluorescence technique.

There is also the problem of finding a new device, enabling to implement such a method.

DESCRIPTION OF THE INVENTION

An embodiment first relates to a method for processing data relating to at least one optical marker in a diffusing medium, wherein:

a) at least one acquisition of a time resolved optical signal is performed, this signal resulting from an excitation of the medium using a pulsed radiation source, each acquisition including on the one hand a component of interest, due to said marker, and on the other hand a spurious component, b) a matrix X is made from each acquisition performed in step a).

Then, the data of said matrix X can be processed by factorizing this matrix into a product of two non-negative matrices A and S.

It is then possible to extract, or to determine or calculate or identify, the contribution of one of said components to at least one of said acquisitions, from terms of the matrices A and S.

According to one embodiment, such a method can further include a step of calculating or determining or identifying or locating the position of at least one optical marker in the diffusing medium and/or a graphical representation of the distribution of at least one such marker in the diffusing medium, from at least one of said acquired time components.

According to this embodiment, the contribution to the detected signal can be identified, but also the position (even approximately) of one of more optical markers in the studied diffusing medium, into three dimensions, without using, or resorting to, a spectral decomposition of the fluorescence radiation, and without requiring time measurements intended to only represent the spurious signal (without the marker).

A marker can be a molecule having the desired optical properties.

According to one embodiment, at least one of the optical markers is a fluorescent marker.

In this case, during the step a), a fluorescence signal is detected, a wavelength of which corresponds to at least one wavelength of at least one fluorescent marker, the diffusing medium being then excited by a pulsed radiation source, the source emitting at an excitation wavelength of the marker fluorescence.

The component of interest, due to at least one of the fluorescent markers, is then at least one fluorescence component (but there can be several ones).

The spurious component can comprise an auto-fluorescence component of the medium, as well as a diffusion component of the excitation light.

Then, a fluorescence contribution due to at least one of the fluorescent markers can therefore be extracted or calculated or determined or identified from terms of the matrices A and S.

Then, the position of at least one of the fluorescent markers can be determined or calculated, in the diffusing medium and/or a graphical representation of a distribution of one or more fluorescent markers, from a fluorescence contribution obtained during step d).

According to another embodiment, at least one of the optical markers has absorbance and/or diffusion properties different from those of the medium in which it is placed. At least one of the component of interest consequently includes an absorbed and/or diffused radiation.

In this case, the detected radiation is a diffusion radiation emitted by the medium, responsive to a pulsed luminous excitation. In this case, the radiation diffused by the marker has time characteristics different from those of the radiation diffused by the medium.

The position of at least one of the markers, in the surrounding medium and/or a graphical representation of a distribution of one or more markers can then be determined or calculated, from the components of interest.

Said method can further include, before said multidimensional array is formed, a step for correcting the optical signal data of each acquisition by recentring the time data in a time range around an average time of the optical signal.

In either method above, the first non-negative matrix A of the product AS can be a matrix the elements $a_{x,p}$ of which are weighting coefficients, $a_{x,p}$ being the contribution, in one acquisition indexed by the index $x$, of a component of interest, for example of fluorescence, or of a diffusion and/or auto-fluorescence component, these components being designated by the index p.

The second non-negative matrix S can include the time profile of interest, for example of fluorescence, of each component.

Each row p of this matrix can represent a signal time profile peculiar to the component p (digitized value of this time profile). The number of rows of the array S and the number of columns of the array A then correspond to the number of components to be separated.

The array X is formed by performing successive acquisitions, wherein one acquisition can for example correspond to a given position of the source and a given position of the detector, or to the position of a given source and the position of a given detector (herein and in the rest of the text, the position of the source (of a detector respectively) can be the position of the distal end of a fibre which transmits a radiation from said source to the studied medium (or from this medium to the detector).

Thus, the matrix X comprises the measured time data, the latter being also called acquisitions, indexed by the index x and noted $X_x$. Each acquisition corresponds to a time histogram of the signal detected by the detector.

The matrices X, A and S are generally of dimension 2.

During the step of processing the array X comprising the measured time data, the latter being also called acquisitions, A and S can be determined by minimizing a cost function F, wherein this function can be:

the square of the Euclidian distance between the matrix X and the matrix product A·S: then it follows $F=\|X-AS\|^2$ or even the function:

$$F=\|X-AS\|^2+\alpha\|S-S_0\|^2$$

Where $S_0$ is the initial matrix of S and $\alpha$ is a so-called regularisation real coefficient.

The matrix X, gathering one or more acquisitions, is preferably processed according to an iterative process. For example, k iterations are performed, the arrays $A_i$ and $S_i$, obtained during the i-order iteration being updated at each iteration. The number of iterations can be determined depending on the evolution of the cost function F between successive iterations, or depending on the value of this cost function, by then comparing it to a predetermined stop criterion. In other words, in the latter case, the iterative process stops when the cost function reaches said stop criterion. The number of iterations can also be empirically determined, depending on the user experience.

The excitation of the medium can be performed by a laser excitation source, which may be possibly focused at the interface between the diffusing medium and the external medium. The excitation light will then penetrate the diffusing medium, and excite therein markers or sources in this medium, for example at 3 cm or 5 cm deep, that is at a distance from the interface, into the diffusing medium. The fluorescence radiation therefore comes from a depth area, for example between the interface and about 3 cm or 5 cm away from the interface, or between 1 cm at a distance from the interface and 5 cm away from the interface. The excitation can occur in the infrared or near infrared or red, for example at a wavelength between about 600 and 900 nm. According to one embodiment, the fluorescence of a fluorescent marker can be detected at wavelengths higher than the excitation wavelength of the medium.

Another aspect concerns a device for locating an optical marker in a diffusing medium, or for processing data relating to such a marker, including:

a) at least one pulse radiation source to generate an excitation beam of the diffusing medium, b) means for performing at least one acquisition of a time resolved optical diffusion signal of at least one optical marker of said medium, the acquisition including on the hand one or more components of interest, and on the other hand one or more spurious components, c) means for making up a matrix X from each acquisition, d) means for processing data of said matrix X by factorizing into two non-negative matrices A and S, e) means for calculating or determining or identifying or extracting the contribution of one of said components to at least one of said acquisitions from terms of the matrices A and S.

According to one embodiment, such a device further comprises means for determining or calculating or identifying and/or viewing the distribution of intensities of the optical marker(s) from at least one contribution of one of said components.

The optical marker can be a fluorescent marker. In this case, the component of interest associated with this marker is a fluorescence component. Then, the excitation source generates pulses at the excitation wavelength of the fluorescent marker, and the detection means are adapted to collect the fluorescence radiation of the fluorescent marker.

According to this embodiment, the excitation source enables the medium to be lighted, and an area, called excitation area to be generated in the latter. Indeed, the excitation light penetrates the medium, diffuses therein, and excites the fluorescence sources, markers and auto-fluorescence tissues. As explained above, the fluorescence sources can be located in depth, at a distance under the interface.

Said device can further include means for changing the position of the excitation source and/or detection means. An acquisition of the time resolved diffusion optical signal, for example a fluorescence signal, can be performed for each position of the excitation source and the detection means.

Said device can include several optical fibres which enable the radiation of the excitation source to be brought into different points of the medium and/or various optical fibres which enable to sense, at different points of the medium or at different points of its limit, an optical radiation, for example a fluorescence radiation, which comes from this medium, and to bring it to one or more detectors.

Said means for processing the acquisition matrix X by factorizing into two non-negative matrices A and S can implement a method as already described above.

DETAILED DESCRIPTION OF EMBODIMENTS

In this description, the case where the optical marker(s) is (are) fluorescent marker(s) will be first considered.

Figures 1, 2A, 2B:
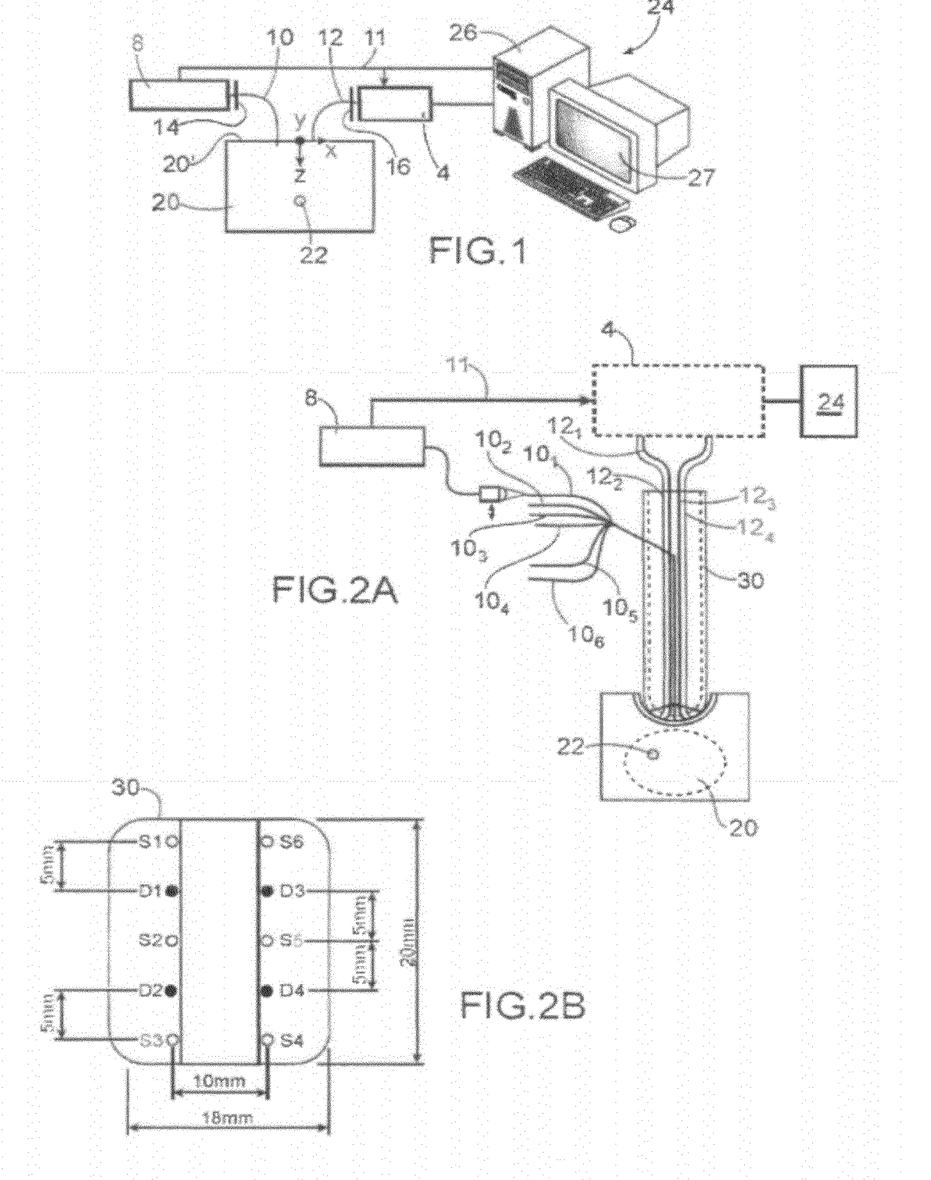
FIG. 1 represents a device for implementing one embodiment.
FIGS. 2A and 2B represent another device for implementing another embodiment.

FIG. 1 shows an experimental system which can be implemented according to this document.

The illumination of a medium 20 to be examined is performed using a radiation source 8 which generates radiation pulses, for example a radiation in infrared or even near infrared. This radiation source is pulsed, each radiation pulsed can have a full width at half-maximum between, for example, a few nanoseconds, for example 1 ns or 10 ns, and a few femtoseconds, for example 10 fs.

It can be for example a laser operating in a pulsed manner. The beam of this radiation source can be directed toward the medium, for example with an optical fibre 10.

Alternatively, several fibres can be used to send pulses at various places in the medium, then defining as many light sources, wherein each fibre end can be assimilated to a light source S. Switching means, for example a translation stage, then enable a fibre to be selected from the different fibres.

A stage enables the radiation source to be positioned in front of any fibre.

The excitation radiation preferably passes through an interference filter 14 to remove most of the light at a wavelength higher than the excitation wavelength.

The excitation light diffuses in the diffusing medium 20 and will excite therein one or more fluorescent species.

In response, the medium emits radiation comprising:
- a fluorescence component, due to the presence of the fluorescent marker(s) 22, this component being sometimes called specific fluorescence because it comes from the fluorescent markers. This is the component, which determination is generally attempted, so as to locate the position of the fluorescent markers in the medium;
- a spurious (or noise) component; the latter can in particular include an auto-fluorescence component of the medium and/or a diffusion component of the excitation radiation in the medium and/or one or more spurious components due for example to the specific fluorescence of some hardware elements of the system, for example optical components.

One or more fibres 12 collect the light from the studied medium 20, called emitted light. An interference filter 16 and/or a coloured filter can be placed in front of the detector 4 to limit the light detection outside the fluorescence spectrum of the fluorophores 22 provided in the medium 20 and optimize the elimination of the excitation light. The filter can for example be a high-pass filter, passing the wavelengths higher than 650 nm when the source emits at the wavelength 631 nm.

The radiation emitted is thus sent to detection 4 and acquisition 24 means. The detection means 4 comprise a photon detector, connected to means for acquiring the detected signal, the latter can include acquisition boards or cards of a computer.

These acquisition means 24 enable the time distribution of a signal detected by the detection means 4 to be obtained. By time distribution, it is meant the time, called arrival time, separating the detection of a photon from a determined initial time $t_0$. This initial time generally corresponds to the instant $t_{imp}$ when the source emits a luminous pulse, possibly with a slight time shift. Such a distribution is generally discretized in time and is in the form of a histogram commonly called by the acronym TPSF (Temporal Point Spread Function). Generally, the detection and acquisition means enable a time resolved fluorescence signal to be obtained, this signal generally having the form of the histogram previously described.

The emitted radiation is possibly transmitted to the detection means 4 via one or more optical fibres 12, as already explained above. In this case, the end of each optical fibre located on the diffusing medium side can be assimilated to a detector.

The detection 4 and acquisition 24 means include for example a photomultiplier coupled to a counting board or card; the latter generating a time distribution of the signals detected by the photomultiplier.

The detection 4 and acquisition 24 means can also include an intensifier rapid camera, this camera being activated according to a time gate, the opening of which is successively shifted, which enables a TPSF type histogram to be simultaneously performed at different space points.

A synchronization line 11 enables the detection 4 and/or acquisition 24 means to be triggered using a pulse generated by the radiation source 8.

Thus, these detection 4 and acquisition 24 means enable a time resolved fluorescence signal or time histogram of the fluorescence signal to be obtained. When the medium is excited by a source s and the signal emitted by the medium is detected by the detector d, this histogram is noted $X_{sd}$. It can also be called time resolved acquisition corresponding to the source-detector couple. Thus, a time resolved acquisition can be referenced as $X_x$ or $X_{sd}$, the index x being an integer with $1 \leq x \leq Nx$, the index sd representing a source-detector couple.

This means 24 include means for digitizing the fluorescence time data. Data processing means 26 will enable processing. These electronic means 24 include for example a computer or a microcomputer or a microprocessor programmed to store and process data acquired by the means 4. They can also include synchronization means for synchronizing the acquisition of the signal detected by the detector 4 and pulses from the pulsed source 8. A central processing unit 26 is programmed to implement a processing method as disclosed herein. Displaying or viewing means 27 enable, after processing, to represent the positioning or spatial distribution of fluorophores in the medium being examined. The means 4, 24 possibly enable to control or monitor other parts of the experimental device, for example the selection of the position of the source and/or the detector, for example again via the position of a stage or an optical switch.

The studied medium 20 is a diffusing medium, for example a biological tissue. An excitation incident radiation can penetrate this kind of medium, wherein the penetration depth can reach a few cm depending on the extinction coefficient of this medium, for example 3 cm or 5 cm.

In other words, it will be possible to detect fluorophores located at a distance z from the medium boundary 20' between 0 cm (therefore located very close to the surface) and, for example 3 cm or 5 cm.

The detection 4 and acquisition 24 means determine the time distribution $X_{sd}$ of a radiation which comes from the area of the diffusing medium excited by the light source s, which passes through the diffusion medium toward the boundary 20' between the diffusing medium and the external medium, and then reaches the detector means 4 comprising the detector d. A spectral analysis is not necessary for the purposes of the present embodiment.

Typically, the studied medium can be a living medium. It can be for example an area of a human or animal body. The body frame is the interface of the diffusing medium with the external medium. An excitation source is thus focused on this interface, or into the medium. Markers injected beforehand into this diffusing medium enable areas such as tumours to be located.

As already explained above, there is also an excitation of other elements of the medium, providing a spurious component to the signal detected.

Another exemplary device is illustrated in FIG. 2A, in an application to a medium which is indeed a prostate phantom 20 containing fluorescent markers 22. A laser 8 operates which pulses, for example at a wavelength close to 775 nm. The pulses sent are very brief: they are for example in the order of a few tens of picoseconds (for example with a time width at half-maximum between 10 ps and 50 ps).

The output of the laser 8 is fibred and sent into 6 source fibres $10_1, 10_2, 10_3, 10_4, 10_5, 10_6$. These fibres are integrated into an endorectal probe shell 30 in contact with the phantom. For each source fibre ($10_i$, i=1-6), light propagates in the medium 20 to the fluorescent area.

Thus excited fluorescent markers 22 emit photons at a wavelength higher than that of the excitation, herein at about 800 nm. But there is in the signal other spurious contributions, in particular from auto-fluorescence which comes from biological tissues surrounding the fluorescent markers. By using a phantom such as the one represented in FIG. 2A, it is possible to obtain an auto-fluorescence signal by performing the subtraction of two acquisitions respectively carried out with and without the fluorescent inclusion.

This probe also contains 4 detection fibres $12_j$ (j=1-4) for collecting the fluorescence signal. These fibres convey the detected light to the detector d included in the detection means 4, connected to a photon counting board or card, being part of the acquisition means 24, which enables the construction of the photon arrival time histogram or photon time distribution. The detection 4 and acquisition 24 means have already been described above. Filters can also be used, as already explained above.

FIG. 2B represents the end 30' of the probe 30, with the ends $S_1$-$S_6$ of the excitation fibres $10_i$, i=1-6 and those ($D_1$-$D_4$) of the detection fibres $12_j$ (j=1-4).

By way of example, the end of the probe 30 can have a substantially rectangular cross-section, for example with a side of 20 mm and 18 mm. The ends of the excitation and detection fibres are distributed along two rows, alternately on each row, between the excitation fibres and the detection fibres, for example at a pitch of about 5 mm. Therefore, on each row, there are the ends of 5 fibres, among which 3 excitation fibres and 2 detection fibres.

For each excitation fibre $10_i$, i=1-6, it is possible to carry out, measurements for each detection fibre $12_j$ (j=1-4).

Thus, in the example of 6 excitation fibres and 4 detection fibres, it is possible to carry out 4 measurements (one of each detection fibre $12_j$ (j=1-4)) with one excitation by the fibre $10_i$, i=1-6 (i=1-6).

In the description that follows, the term source designates both a non-fibre source, or the end of the excitation fibre when the source is fibred. Furthermore, the term detector designates both a detector, a group of pixels of a pixelized detector or the end of a detection fibre, optically coupled to a detector.

In the following (or on the figures) by "source n, detector p" (or $s_n$, $d_p$) it is meant an acquisition obtained by excitation via the excitation source $10_n$ and by detection via the detector $12_p$. Also, each acquisition is noted $X_{s_n d_p}$. In the description that follows, $X_{s_n d_p}$ is a row vector, each row including data representing the fluorescence time histogram, that is a time distribution of detected photons. $X_{s_n d_p}$ could also be represented as a column vector.

Each acquisition $X_{s_n d_p}$ consists of terms noted $X_{s_n d_p, t}$ representing the time discretization pitch, with $1 \leq t \leq N_t$. $N_t$ is the maximum abscissa of one histogram, generally corresponding to an arrival time of a few ns to about 10 ns.

Each acquisition could also be indexed by an index x, and would then be noted $X_x$, with $1 \leq x \leq N_x$, $N_x$ being the total number of acquisitions assembled in the acquisition matrix X.

In the case of FIGS. 2A and 2B, 4×6=24 acquisitions are thus obtained.

For each configuration, corresponding to a source-detector couple, the following are measured:
  a so-called raw fluorescence acquisition, coming from the medium with the fluorescence inclusion; the term raw indicates the fact that the detected signal comprises a fluorescence component, or component of interest, and a spurious component. This time resolved signal corresponds to the acquisition $X_{sd}$,
  an acquisition consisting only of said spurious component, this signal being measured without the fluorescent inclusion; it should be noted that the determination of such a component is generally not possible, because it is not possible to withdraw the fluorescent markers from the medium,
  an acquisition $X_{diff}$ consisting of the diffusion of the excitation signal in the medium (at the excitation wavelength, without fluorescence filter).

Figure 3A:
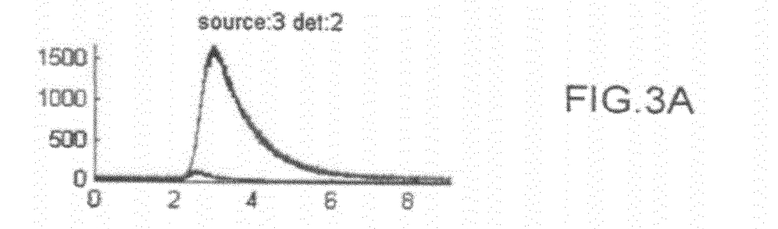
FIGS. 3A-3B represent acquisitions, on the one hand of the raw fluorescence measured and, on the other hand, of a measured spurious signal, for two source-detector couples.
Figure 3B:
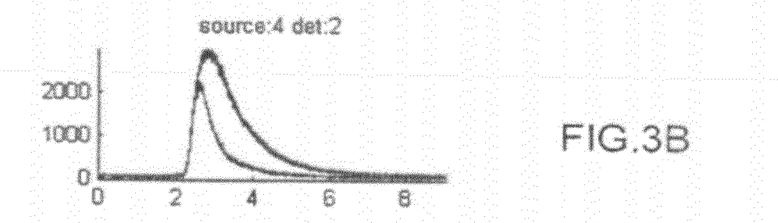

Some exemplary acquisitions obtained with this device are illustrated in FIGS. 3A-3B:
  for the source 2 and the detector 2 (FIG. 3A),
  for the source 4 and the detector 2 (FIG. 3B).

Each figure simultaneously shows the raw fluorescence (time resolved) signal and the spurious (time resolved) signal. The latter is sometimes low compared to the raw fluorescence signal (case of FIG. 3A) but sometimes significant (case of FIG. 3B). It can be seen that there is actually a disturbance in the fluorescence signal measurements by the auto-fluorescence and/or diffusion spurious signals.

To deal with this problem, first a retiming of the time acquisition data of the raw fluorescence signals $X_{sd}$ can be performed with respect to a pulsed response time.

This correction step is optional, but will be preferably performed. The inventors have indeed found that such a retiming of each acquisition $X_{sd}$, performed prior to decomposition of the matrix X, enables results of the factorization of this matrix to be improved.

One object of this retiming can be to get rid of variations in the pulsed response functions of the device, or of both the device and the medium, between the different source-detector couples.

Indeed, in a configuration such as described in FIG. 2A, the sources and the detectors are fibred. Depending on the length of an excitation fibre $10i$ separating the laser 8 from the end of the probe 30, depending on the length of an emission fibre $12i$ extending from the end of the probe 30 to the detection means 4, and depending on the positions of the ends of said excitation $10i$ and emission $12i$ fibres on the probe 30, a same laser pulse will not be detected at the same time whether an emission fibre-detection fibre couple (or source-detector couple) or another couple is used. Thus, it is useful to lower the time shifts between the different source-detector couples when the medium is excited by a same pulse.

In order to correct such a shift for example, first the pulsed response time T_$diff_{sd}$ of the diffusion signal measured can be calculated:

$$\mathrm{T\_diff}_{sd} = \frac{\int_0^\infty X_{diff_{sd}}(t) t \, dt}{\int_0^\infty X_{diff_{sd}}(t) \, dt}$$

Thus, to each source-detector couple corresponds an average time of the diffusion signal T_$diff_{sd}$.

This average time quantizes, for a given source-detector configuration, the average duration between the light emission and the diffusion photon detection by the detector.

During such an acquisition, the filter 16 provided upstream of the detector 4 can be withdrawn, such that the detection means 4 detect a signal at the excitation wavelength, and not at the fluorescence wavelength as will be the case during fluorescence acquisitions.

Then the theoretical average time of the diffusion signal can be calculated, in the diffusing medium, called $\hat{T}\_diff_{sd}$, predicted by the chosen diffusion model (the "hat (^)" designates the model, as opposed to the measurement). For example, in an infinite medium, this average time is determined by dividing the distance between a source and a detector by the velocity of light in the medium. It will be reminded that by source and detector, it is meant here an end of the excitation fibre $10i$ and an end of the emission fibre $12i$, both ends being secured to the probe 30. In this case, $\hat{T}\_diff_{sd}$ is digitally calculated. To do this, the following equation can be digitally resolved:

$$-\vec{\nabla} \cdot \left(D\vec{\nabla} G_s^{(1)}\right) + \mu_a G_s^{(1)} = \delta(\vec{r} - \vec{r}_s) + \frac{G_s^{(0)}}{c}$$

With $G_s^{(1)\circ}$=1-order moment of the Green function expressing the energy transfer between the source and the detector;

$G_s^{(0)}$=0-order moment of the Green function expressing the energy transfer between the source and the detector;

$\mu_a$: absorption coefficient of the diffusing medium c: velocity of light

D: diffusion coefficient of the medium $r_s$: coordinates of the source, the latter can be assimilated to the end of the emission fibre when the source is fibred.

Finally, $T\_impulse_{sd}$ is defined as the difference between two previously defined times:

$$T\_impulse_{sd} = T\_diff_{sd} - \hat{T}\_diff_{sd}$$

$T\_impulse_{sd}$ represents the pulsed response time of the device, that is the average time elapsed between a pulse of the source and the detection of photons diffused by the diffusing medium. This average pulsed response time quantizes the time period between the emission of a pulse and the detector of a diffusion signal, corrected by the estimation of the diffusion time period in the medium. In other words, $T\_impulse_{sd}$ quantizes the pulsed response time of the device, whereas $T\__{diffsd}$ quantizes the pulsed response time of the device and the diffusing medium taken together.

Generally, it will be remembered that $T\_impulse_{sd}$ and $T\__{diffsd}$ are pulsed response times, quantizing an average time period between the emission of a pulse and the detection of a detection signal.

The retiming of measured data can be made with respect to a pulsed response time, which may be either $T\__{diffsd}$, or preferably $T\__{impulse\_sd}$, such as previously defined.

The purpose of retiming is to allow thereafter each acquisition $X_{sd}$ to be represented along a time axis, such that each pulsed response time considered corresponding to the sd configuration has a same coordinate along the time axis. In other words, if X'sd designates an acquisition $X_{sd}$ retimed with respect to a pulsed response time, then:

$$X'_{sd}(t) = X_{sd}(t - T\_impulse_{sd})$$

or $$X'_{sd}(t) = X_{sd}(t - T\_diff_{sd})$$

In other words, each acquisition $X_{sd}$ is retimed according to the pulsed response time, determined for each source-detector configuration.

This can also be considered as a centring of each acquisition $X_{sd}$ depending on the pulsed response time corresponding to the source-detector sd couple: indeed, according to the previous equation, for each source-detector couple, $X_{sd}'(T\_impulse_{sd})=0$ (or $X_{sd}'(T\_diff_{sd})=0$.

In this way, the retimings between the time resolved signals corresponding to each source-detector couple are restricted.

In the description that follows, the factorization of the acquisition matrix X, consisting of a plurality of acquisitions $X_{sd}$ will be more precisely described. The method described is indifferently applicable to a matrix X consisting of acquisitions $X_{sd}$ whether retimed or not. Preferably, the acquisitions $X_{sd}$ are retimed according to the previous equation.

Figure 4:
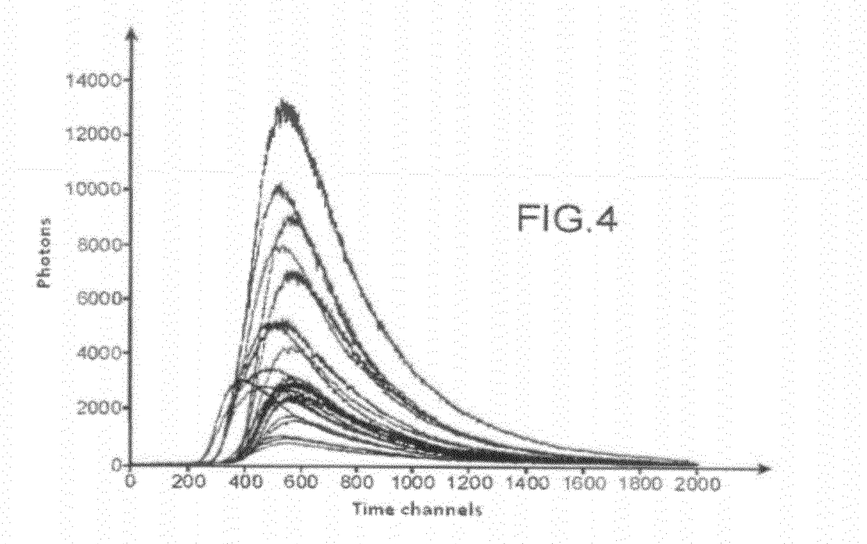
FIG. 4 is an exemplary superimposition of a raw fluorescence acquisition assembly, for 6 sources and 4 detectors, FIG. 5 schematically represents the decomposition.

FIG. 4 is an exemplary superimposition of a set of 24 fluorescence measurements $X_{sd}$, for 6 sources and 4 detectors. The acquisitions are retimed, as explained above, with respect to the average time of the diffusion measurement.

There remain shifts between the time positions of the different peaks, due to the relative positions of the source-detector couples and fluorescent markers: the path between the end of an excitation fibre and a marker is not the same than that between the end of another excitation fibre and the same marker, and the problem is the same with the different positions of the detectors (or of the ends of the detection fibres) with respect to the same marker.

It will now be explained how to exploit this data, preferably corrected or recentred, in order to make an image of the fluorescent markers in the medium. The previous (optional) step enables the data to be recentred without getting rid of auto-fluorescence or, more generally, of the spurious signals, whereas the following steps enable these components to be separated.

In the description that follows, it is assumed that each acquisition is a time corrected acquisition. But it is not always necessary to implement such a correction.

Let us consider a fluorescence acquisition $X_{sd}$ (that is a set of data resulting from sampling a fluorescence curve such as one of those of FIGS. 3A-3B) from a diffusing medium containing a fluorescent marker type.

This measurement is the superimposition of two distinct time distributions:

$S_1$: time distribution of photons of interest emitted by the fluorescent markers, called fluorescence time component or component of interest, $S_2$: time distribution of so-called spurious photons, including auto-fluorescence and/or diffusion photons, called spurious time component.

If the respective amounts of this distributions are written as $a_1$ and $a_2$, the acquisition $X_{sd}$ can be written as the following linear combination of the 2 distributions $s_1$ and $s_2$:

$$X_{sd} = a_1 s_1 + a_2 s_2 = (a_1 \quad a_2) \times \begin{pmatrix} s_{1,1} & \cdots & s_{1,N_T} \\ s_{2,1} & \cdots & s_{2,N_T} \end{pmatrix} = AS \quad (1)$$

Where each term $S_{p,t}$ of the matrix S is the profile value of the component p corresponding to the time interval t. Each time interval t generally corresponds to the time sampling frequency implemented during the acquisition $X_{sd}$.

Thus:

$s_{1,i}$ designates the ith value of the distribution $s_1$, $s_{2,i}$ designates the ith value of the distribution $s_2$.

According to this method, finding matrices A and S with non-negative coefficients is attempted, the product of which is as close as possible to the matrix $X_{sd}$.

This exemplary data processing can be generalized to a series X of $N_x$ acquisitions. X is then a non-negative matrix $X \in R^{N_x \times N_T}$, each term $X_{x,t}$ of which corresponds to the value of the acquisition $X_x$ in the time channel t. As previously indicated, the index x can be replaced by the index sd, the latter representing the position of a source s and a detector d. $N_x$ then represents the number of source-detector couples considered.

Then finding the non-negative matrices $A \in R^{N_e \times N_p}$ and $S \in R^{N_p \times N_t}$ is attempted such that:

$$X \approx AS \quad (2)$$

By non-negative matrix, it is meant a matrix all the elements of which are non-negative, and Np represents the number of time components, or of time distribution $s_i$, being searched for.

A is called a weight matrix. An element $a_{sd,p}$ ($\geq 0$) of this matrix represents the contribution, in a fluorescence acquisition $X_{sd}$, of a fluorescence time component or a diffusion and/or auto-fluorescence time component, these components being designated by the index p (for example p=1 designating the fluorescence component and p=2 designating the spurious component).

S is the matrix of components of X to be separated from each other (in this example, fluorescence component or spurious component), each row of this matrix, noted $S_p$, including discretized data representing a time profile for the component p.

Figure 5:
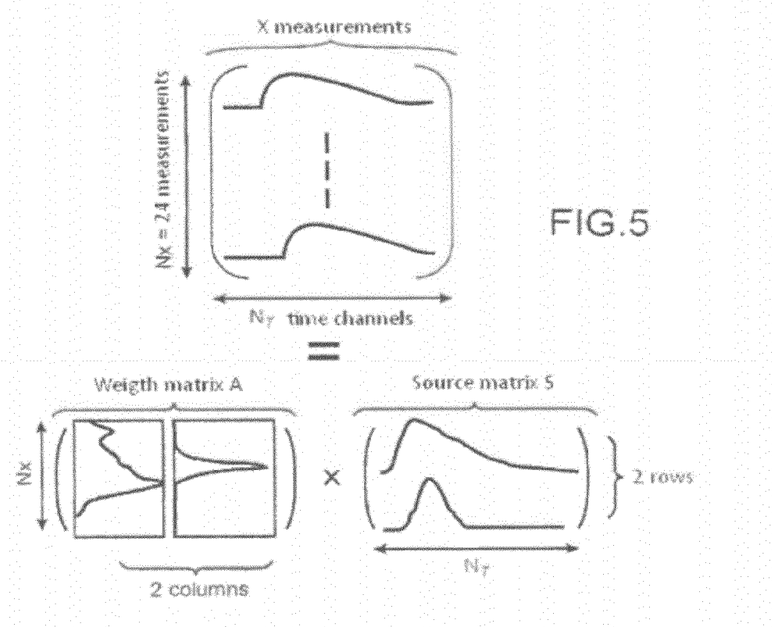

If only 2 time components (p=2) are considered, this equation can be illustrated according to the schematic diagram of FIG. 5 for the case of 24 measurements.

The problem is then to find particular matrices A and S to meet the above equation.

For this, it is attempted to minimise a cost function F, for example the square of the Euclidian distance between X and AS, or an adaptation of the Kullback-Leibler divergence. Another expression can also be used, including the square of said Euclidian distance, detailed in the description that follows.

If the Euclidian distance between the matrix X and the product of both matrices A and S are considered, then it is attempted to minimize the cost function F:

$$\|X-AS\|^2$$

with $A \geq 0$ and $S \geq 0$.

The solution is obtained in a approximate manner, by iterations.

Different methods can be used to minimize the cost function. There can be mentioned the multiplicative updated laws introduced by Lee and Seung in the article *"Learning the parts of objects by non negative matrix factorization"* published in Nature, pages 788-791, 1999. According to this technique, the general optimization procedure can thus consist of:

1. Initializing A and S by positive random values,
2. Updating A
3. Updating S
4. Repeating steps 2 and 3 until the cost function F, or its variation between two successive iterations, reaches a convergence criterion, or up to a number of iterations.

In the case of $N_x$ acquisitions (for example: all the 24 measurements obtained with the device of FIGS. 2A and 2B), each being discretized along $N_t$ time points, thus there is:

$$X = \begin{pmatrix} x_{11} & \cdots & x_{1,Nt} \\ \vdots & \ddots & \vdots \\ x_{Nx,1} & \cdots & x_{Nx,Nt} \end{pmatrix} = \begin{pmatrix} a_{11} & a_{12} \\ \vdots & \vdots \\ a_{Nx,1} & a_{Nx,2} \end{pmatrix} \begin{pmatrix} s_{11} & s_{1,Nt} \\ s_{21} & s_{2,Nt} \end{pmatrix}$$

If the index p=1 designates the fluorescence time component, and the index p=2 designates the spurious time component, then the product $a_{x,1}*S_1$ corresponds to the histogram of the fluorescence time component corresponding to the acquisition $X_x$.

This fluorescence time component can be noted $I_x$ (or $I_{sd}$ when the index designates a source-detector couple). This component $I_x$ corresponds to the acquisition $X_x$ corrected for its spurious component. In other words, $I_x$ represents the part of $X_x$ actually due to fluorescent markers, hence the designation component of interest. It can also be written that $I_x$ represents the fluorescence "net" signal, whereas $X_x$ represents the fluorescence "raw" (i.e. not corrected) signal.

The product $a_{x,2}*S_2$ in turn corresponds to the spurious time component of the acquisition $X_x$.

The equation already presented above is well recognized: $a_{x,1}*S_1 + a_{x,2}*S_2 \approx X_x$.

Consequently, it can be seen that from the matrices A and S, a time component, designated p, of one acquisition $X_x$, is obtained by multiplying the terms of the row $S_p$ by the coefficient (or weight) $a_{x,p}$. Depending on the value p, this component can be a component of interest (fluorescence component in this example) or a spurious component.

More generally, this component p is obtained by multiplying terms of the matrix S, relating to this same component, by the term $a_{x,p}$, of the matrix A, representing the weight of the contribution p in the histogram $X_x$.

In FIG. 5 the pictorial example of the product of a matrix S (for an acquisition with two fluorescent sources) is given with an array A in order to obtain the array X.

An exemplary cost function F to be minimized has been given above. But this can have different forms. The square of the Euclidian distance between X and AS can also advantageously be used, plus a constraint term:

$$F = \|X-AS\|^2 + \alpha \|S-S_0\|^2 \quad (1)$$

Where $S_0$ is the initial matrix S, as explained below, and $\alpha$ is a so-called regularisation parameter. The latter enables the solution S to be more or less constrained to keep close to the selected initialization $S_0$. Using such a cost function enables the robustness of the method to be increased. This also enables the convergence rate to be increased.

One exemplary algorithm that can be used to calculate the couple of matrices A and S the product of which best represents the initial data X is then once again, an iterative algorithm. The number of iterations $N_{it}$ is determined either empirically, or by a selected stop criterion, as previously discussed.

The algorithm comprises the following steps:

1. Initializing the matrices A and S with strictly positive values. Initializing S can be chosen to be performed with source models experimentally measured or from literature.

2. Selecting the regularization parameter $\alpha$. The selection is empirically made depending on the trust given to the initializing (the greater $\alpha$, the more the calculated matrix S is constrained to be close to the initializing).

A and S are then updated, in turn for $N_{it}$ iterations.

Several methods can be implemented for this updating. For example, a decreasing gradient alternately on A and S (called "ALS" for "Alternative Least Square") can be mentioned or the multiplicative updating laws indicated by Lee and Seung in the article already cited above.

By drawing inspiration therefrom, and defining $X^T$ as the transpose of a matrix X, if the cost function to be minimized is $F=\|X-AS\|^2+\alpha\|S-S_0\|^2$, which is the preferred alternative, each iteration comprises the following updatings for A and S:

$$S_{i+1} \leftarrow S_i \frac{(A_i^T X + \alpha S_0)}{(A_i^T A_i S + \alpha S_i)}$$

and then:

$$A_{i+1} \leftarrow A_i \frac{(X S_{i+1}^T)}{(A_i S_{i+1} S_{i+1}^T)}$$

This particular updating laws have been developed by the inventors.

A more conventional, previously discussed, cost function F can be chosen such that $F=\|X-AS\|^2$.

In this case, at each iteration, the updating laws are those described by Lee and Seung:

$$S_{i+1} \leftarrow S_i \frac{(A_i^T X)}{(A_i^T A_i S)}$$

and then:

$$A_{i+1} \leftarrow A_i \frac{(X S_{i+1}^T)}{(A_i S_{i+1} S_{i+1}^T)}$$

From the data of matrices A and S, for each acquisition $X_x$, a fluorescence component, or component of interest, due to the markers, and noted Ix, can be extracted.

Then, a reconstruction method can be implemented, which is based on the diffusion equation model, for example such as described in J. Boutet et al. in "Bimodal ultrasound and fluorescence approach for prostate cancer diagnosis", J. Biomed. Opt. 14, 064001 (2009).

For each time curve obtained, the 0 and 1-order moments of the corrected fluorescence signal $I_x(t)$ can be calculated:

$$M_x^0 = \int_0^\infty I_x(t) \cdot dt \quad (2)$$

$$M_x^1 = \int_0^\infty I_x(t) \cdot t \cdot dt \quad (3)$$

Obtaining such moments enables the position of fluorophores to be determined, according to techniques such as described, for example, in the article of J. Boutet et al. cited above, or even in the document "Méthodes optiques résolues en temps pour la tomographie de fluorescence dans les milieux diffusants", thesis of Aurélie Laidevant defended on the Oct. 5, 2006 at Université Joseph Fourier—Grenoble—France or even in the application EP10179184 dated Sep. 24, 2010.

In order to test the different steps of a method as disclosed herein, different tests have been carried out.

For each source-detector couple, the comparisons between the measured time signals (minus the spurious diffusion signal) and the signals calculated by the method as disclosed herein have been performed using a fluorescence phantom. Exemplary results are given on FIGS. 8A-8B (FIG. 8A: for the source 3, detector 3 couple, FIG. 8B: for the source 4, detector 2 couple). In these figures, the measured signal corresponds to:
- a first measured signal when a fluorescent inclusion is present in the phantom,
- to which a second signal has been subtracted, the latter being measured when the fluorescent inclusion is withdrawn and thus representing the spurious component.

Figure 8A:
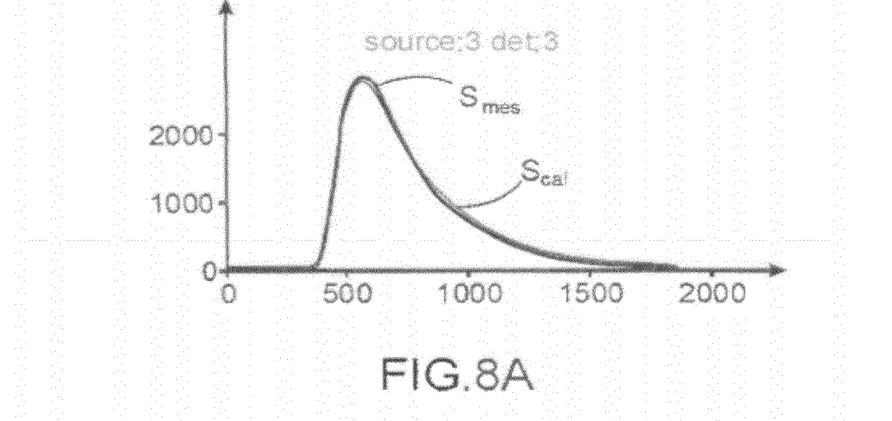
FIGS. 8A-8B and 9A-9B represent comparisons between measured fluorescence components and calculated fluorescence components, as well as between measured and calculated spurious components.
Figure 8B:
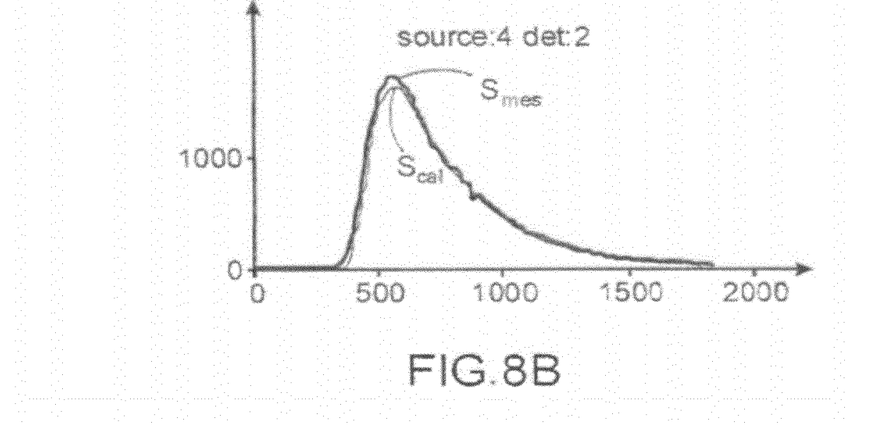

In these figures, the measured signal is identified as $S_{mes}$ and the calculated signal as $S_{cal}$ (fluorescent component of first signal described in the previous paragraph, determined according to the method as disclosed herein). Both signals are nearly superposed or similar.

The subtraction enables the fluorescence component of the first signal to be assessed.

In all the comparisons performed, two examples of which are shown in FIGS. 8A-8B, there is an experimental fluorescence component (measured signal described previously) and a calculated component (calculated signal described previously). In most cases, the values of the measured signal and the calculated signal have a very good matching.

Figure 9A:
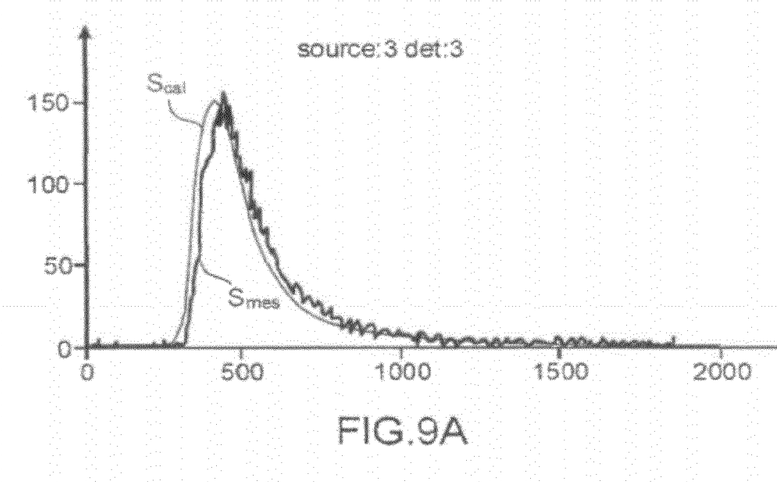
Figure 9B:
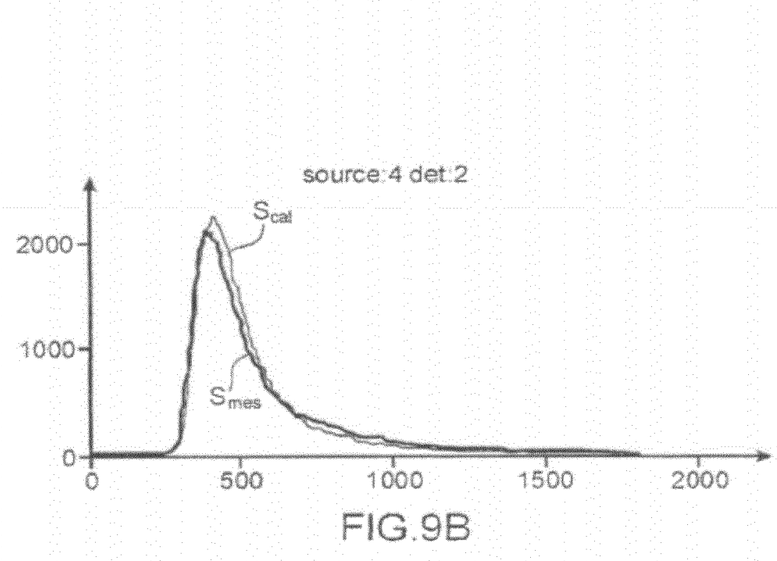

Furthermore, for each source-detector couple, comparisons have been made between the measured spurious signals and the calculated spurious signals by the method as disclosed herein. Two examples thereof are given in FIGS. 9A-9B (FIG. 9A: for the source 3, detector 3 couple; FIG. 9B: for the source 4, detector 2 couple). In each of these figures:

the measured signal $S_{mes}$ corresponds to the measured signal when the fluorescent inclusion is withdrawn. It represents the spurious component;

the calculated signal $S_{cal}$ is the spurious component of a signal measured when the fluorescent inclusion is placed in the phantom. This spurious component is determined according to a method as disclosed herein.

In some cases, and in particular in FIGS. 9A-9B, both signals are virtually confused.

This way an experimental spurious (measured signal described previously) and calculated (calculated signal described previously) component can be obtained.

It has been observed, in most cases, that the measurements and the calculation have a good matching, which allows an experimental validation of the method.

A comparison with results obtained with other methods has been carried out.

Figure 10A:
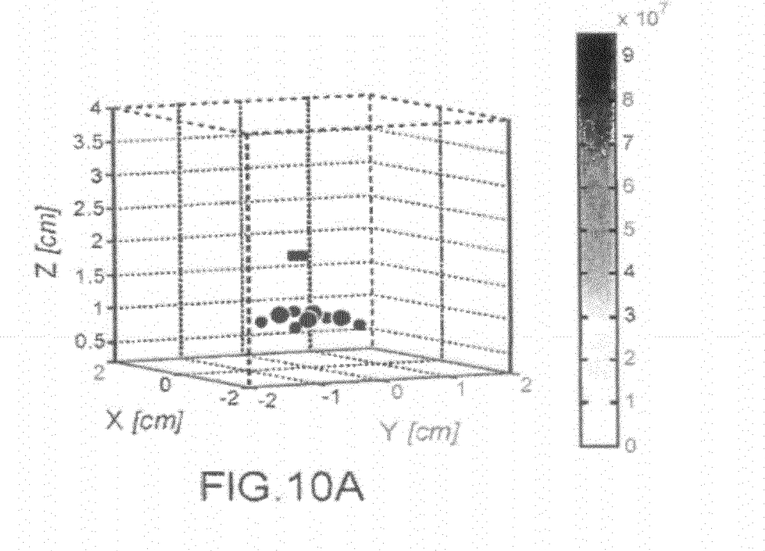
FIGS. 10A, 10B and 11A, 11B represent reconstruction images, on the one hand without correction of the spurious component (FIG. 9A) and then with correction of the spurious component (FIG. 9B) and, on the other hand, with experimental correction of the spurious component (FIG. 10A) and with a correction as disclosed in the present document (FIG. 10B).
Figure 10B:
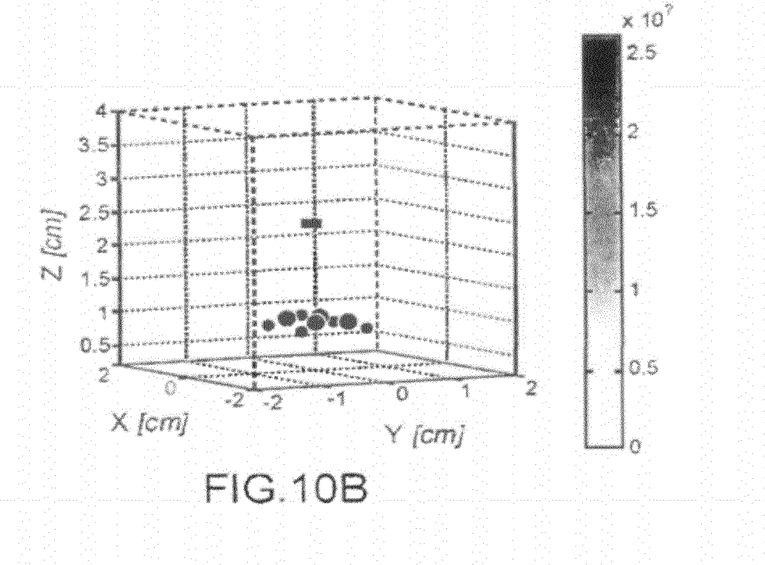

Thus, FIGS. 10A and 10B respectively show a comparison between a localisation by a method without correction and then by a method according to the invention, thus with a correction. In this experiment, the real position of the fluorescent marker along the axis Z, with respect to the limit of the diffusing medium is z=2 cm. By applying a conventional technique and without correction of the auto-fluorescence, z=1.7 cm is obtained (FIG. 10A). With an experimental correction, z=2.12 cm is obtained (FIG. 10B).

During the experimental correction, the spurious component is experimentally determined (measurement without fluorescent inclusion) and it is subtracted from measurements formed with the fluorescent inclusion.

Figure 11A:
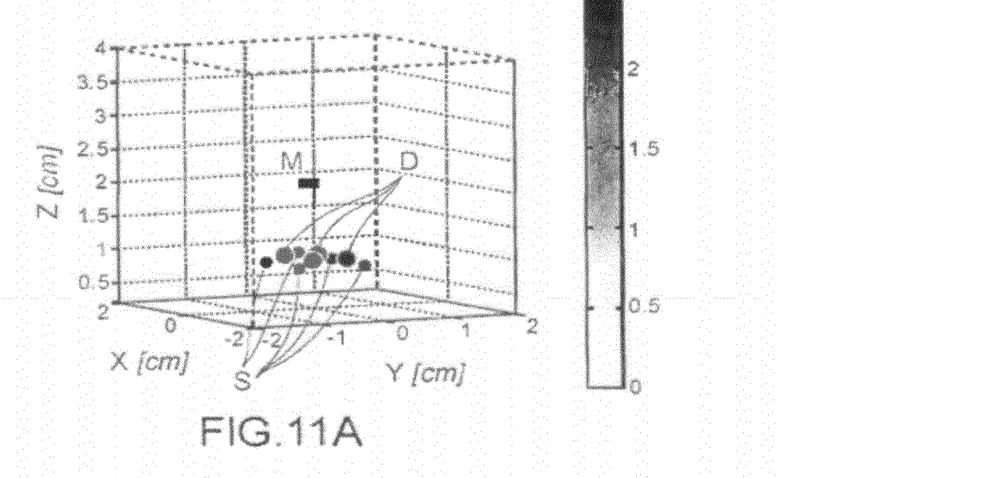
Figure 11B:
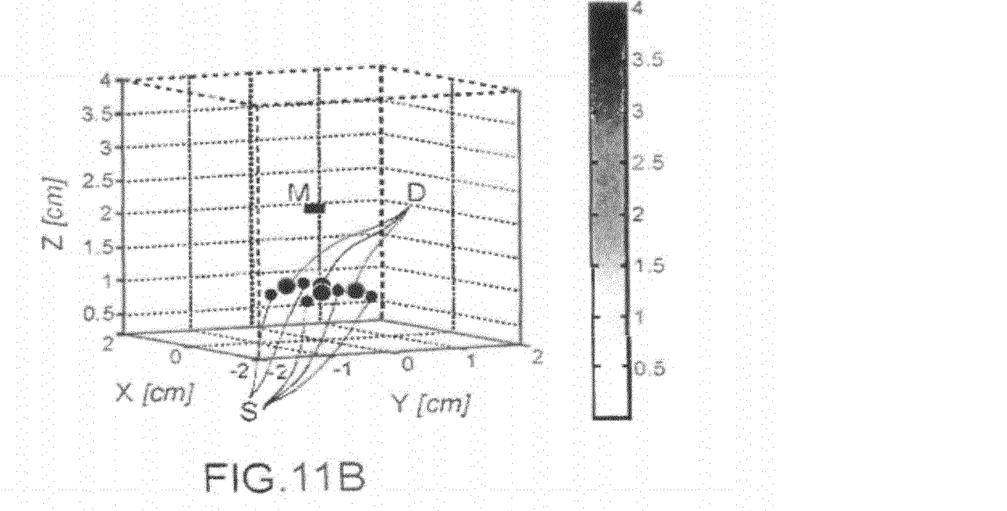

Comparison of FIGS. 10A and 10B shows that, without auto-fluorescence correction, the inclusion is reconstructed at a position too close to the probe (as in FIGS. 11A-11B, the sources S are identified on these FIG. 10 by the low diameter black disks and the detectors d by the higher diameter black disks).

FIGS. 11A and 11B respectively show a comparison between a so-called "experimental" comparison, that is performed by subtracting a measurement on a phantom carried out without fluorescent inclusion from a measurement on the phantom carried out with the fluorescent inclusion and a comparison by a method as disclosed herein.

More precisely, FIG. 11B shows a result obtained with correction by the method for separating the components according to the method previously described using a cost function based on the Euclidian distance for which z=2.19 cm is obtained. The results of the experimental correction (FIG. 11A) and the correction as disclosed herein (FIG. 11B) are similar.

Figure 6:
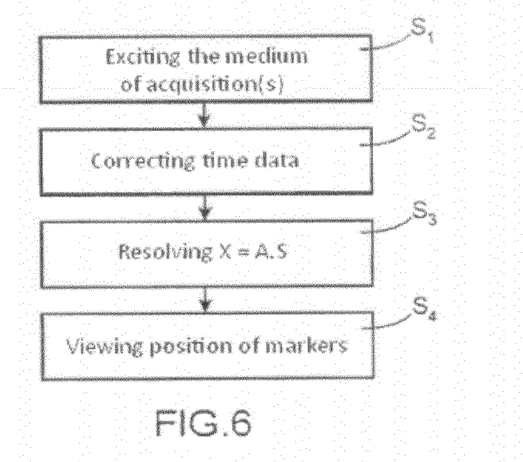
FIG. 6 illustrates how a fluorescence acquisition is made up.

Steps of a method as disclosed herein are represented in FIG. 6:
- in a step S1, one or more acquisitions are performed by exciting the diffusing medium, by a laser beam operating with pulses; resulting in for example one or more acquisitions,
- during step S2, the matrix X is formed with, for each row, digitized and sampled data of a fluorescence signal curve for a couple (source, detector) or a given couple (excitation fibre, detection fibre),
- during an optional step S3, a correction of the time data previously measured for the diffusion signal is performed,
- the equation $X \approx A \cdot S$ can then be resolved, iteratively as explained above (step S4),
- then, the acquisitions corresponding to the component searched for can be determined, in this case the fluorescence component of the markers, then, a graphical representation of the fluorescent marker(s) can be performed (step S5).

When implementing a method as disclosed herein on a patient, the excitation step by the radiation sources can be preceded by an injection step of a fluorescent marker into the medium including the area under study. It is attempted to locate this (these) fluorescent marker(s) in this diffusing medium.

In the entire description above, the acquisitions $X_x$ were represented as a row matrix. But a method as disclosed herein is also applicable when these acquisitions are represented as column vectors. In this case, each column x of the matrix X corresponds to one acquisition, and the contribution of the component p to the vector $X_x$ is obtained by performing the product of the term vector $S_p$ (pth column of the matrix S) by the coefficient $a_{p,x}$. The factorization of the matrix X into non-negative matrices then enables S and A to be determined such that X=S A such that:

X represents the acquisition matrix, with a dimension (Nt, Nx),
S represents the contribution profile matrix, with a dimension (Nt, Np),
A represents the weight matrix, with a dimension (Np, Nx).

Even though in this description two components (a fluorescence component and a spurious component) have been considered, the above teaching is applicable to a higher number of components, for example several fluorescence components and one spurious component, or only several fluorescence components when the spurious component turns to be negligible.

The above teaching is applicable to cases other than those of fluorescent markers.

Indeed, injecting fluorescent markers can have some constraints.

Figure 7:
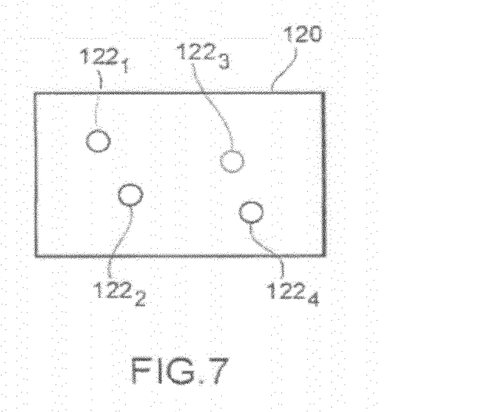
FIG. 7 represents a medium and areas with optical properties different from those of the surrounding medium.

It is sometimes preferable to get rid of it and to aim at locating, in a medium 120 (FIG. 7), not fluorescent markers, but areas 122₁, 122₂, 122₃, 122₄ having optical properties different from those of the surrounding diffusing medium 120. In particular, areas called areas of interest can be searched for, those areas of interest being then considered as optical markers and having:

an absorption and/or diffusion coefficient different from that of the diffusing medium (in this case, a radiation diffused through the tissue is detected, at the excitation wavelength),
and/or a diffusion coefficient different from that of the surrounding diffusing medium; in this case, a radiation, which is diffused differently by the markers and by the diffusing medium, is detected.

The case of absorbing areas, which can be considered as markers, is the one of some cancer tumours.

A method then comprises steps identical or similar to that previously described within the scope of fluorescence, that is:

lighting a diffusing medium by a pulsed excitation light, preferably in infrared or red, in order to restrict absorption into the tissues,
detecting a time resolved diffused signal by the medium, at the excitation wavelength, and performing acquisitions having the form of time histograms $X_x$ of the arrival time of photons, coming from the medium, on the detector,
making up a matrix X gathering one or more ($N_x$) acquisitions $X_x$,
decomposing the matrix X into a product of two non-negative matrices A and S,
determining a component of interest, or useful component, by multiplying terms of the matrix A by terms of the matrix S, for example by multiplying a component $a_{x,p}$ by the terms of the matrix S which are representative of the contribution p.

The useful component $I_x$ to the acquisition $X_x$ then represents the signal diffused by the areas of interest at the excitation wavelength $\lambda_{ex}$. The position of these areas in the medium can then be determined by reconstruction.

An excitation radiation has a wavelength lower than one or more detected wavelengths, regardless of the interaction type between the excitation radiation and the medium, containing one or more markers such as defined above:

if the marker is a fluorescent marker, the fluorescence wavelength is higher than the wavelength of the excitation radiation,
if the marker has an absorption and/or diffusion coefficient different from that of the diffusing medium, then the detected radiation has a wavelength equal to or higher than the excitation radiation.

The invention claimed is:

1. A method for locating at least one optical marker in a diffusing medium, said marker having at least one optical property different from the diffusing medium, the method comprising:

a) producing an optical signal by the pulsed radiation of a pulse radiation source interacting with said medium and said at least one optical marker, and performing at least one acquisition of data of said optical signal, each acquisition including a first time distribution of a component of interest in the optical signal due to said at least one marker and a second time distribution of a spurious component in the optical signal due to said medium other than said at least one marker;
b) forming a multidimensional array X from said optical signal data of said at least one of said acquisitions;
c) processing said array X by factorization into a product of only two non-negative multidimensional arrays A and S; and
d) extracting at least one of said first time distribution and said second time distribution from said arrays A and S.

2. The method according to claim 1, further comprising calculating at least one of:

a position of at least one optical marker in the diffusing medium; and
a graphical representation of the distribution of at least one marker in said diffusing medium, from at least one of said time components.

3. The method according to claim 1, wherein said at least one optical marker comprises a fluorescent marker, excitation of the medium being performed at least at one excitation wavelength of said at least one fluorescent marker, the optical signal resulting from the excitation being at least at one fluorescent wavelength of said at least one fluorescent marker, and wherein at least one time resolved optical signal due to at least one fluorescent marker is extracted from said matrices A and S.

4. The method according to claim 1, wherein said at least one optical marker comprises an area of said medium having at least one absorption and/or diffusing coefficient different from that of said surrounding diffusing medium, said optical signal resulting from the diffusion of said excitation signal into the diffusing medium and wherein at least one time distribution from an area with an absorption coefficient different from that of the diffusing medium is extracted.

5. The method according to claim 1, wherein, before said multidimensional array is formed, the optical signal data of said at least one acquisition are corrected by recentering time data of the optical signal in a time range with respect to a pulse response time.

6. The method according to claim 1, wherein step c) comprises calculating A and S by minimizing a cost function.

7. The method according to claim 6, wherein said cost function is the distance $\|X-AS\|^2$ between the image X and the product A·S.

8. The method according to claim 6, wherein said cost function is the following function:

$$F=\|X-AS\|^2+\alpha\|S-S_0\|^2$$

where $S_0$ is the initial matrix and $\alpha$ is a so-called regularization coefficient.

9. The method according to claim 1, wherein step c) is performed by k iterations, the arrays $A_{l+1}$ and $S_{l+1}$, obtained during the l+1-order iteration being determined from the arrays $A_l$ and $S_l$ obtained during the l-order iteration.

10. The method according to claim 9, wherein a number of iterations is determined depending on fluctuations in the arrays A and S, or automatically depending on fluctuations in the cost function during 2 or more successive iterations.

11. The method according to claim 1, wherein excitation radiation resulting from said pulse radiation has a spectrum at least partly in infrared.

12. The method according to claim 1, wherein said optical signal has a spectrum at least partly at a wavelength higher than 600 nm.

13. A device for identifying at least one optical marker in a diffusing medium, including:
   a) a pulse radiation source generating an excitation beam of said medium and of at least one optical marker;
   b) a detector performing at least one acquisition of optical signal data, each acquisition including a first time distribution of a component of the optical signal due to said at least one marker, and a second time distribution of a spurious component in the optical signal due to a part of the medium other than said at least one, marker; and
   c) at least one processor configured to form a multidimensional array X from said optical signal data, to process said array X into a product of only two non-negative multidimensional arrays A and S and to extract from said arrays A and S at least one of said first time distribution and said second time distribution.

14. The device according to claim 13, said at least one processor calculating at least one of:
   the position of at least one optical marker in the diffusing medium; and
   a graphical representation of the distribution of at least one marker in the diffusing medium.

15. The device according to claim 13, said at least one processor correcting said optical signal data of each acquisition, before multidimensional array is formed, said correcting comprising recentering said time resolved optical signal in a time range around an average time of said optical signal.

16. The device according to claim 13, said at least one processor determining A and S by minimizing a cost function.

17. The device according to claim 13, said pulsed radiation source producing an excitation beam at least partly in infrared.

18. The device according to claim 13, wherein said detector detecting a radiation at least at one wavelength higher than 600 nm.

19. A device for identifying at least one fluorescent marker in a diffusing medium, comprising:
   a) a pulse radiation source generating an excitation beam of said medium and of at least one of said fluorescent marker
   b) a detector performing at least one acquisition of optical signal data, each acquisition including a first time distribution of a component of the optical signal due to said at least one marker, and a second time distribution of a spurious component in the optical signal due to a part of the medium other than said at least one marker; and
   c) at least one processor configured to form a multidimensional array X from said optical signal data, to process said array X into a product of only two non-negative multidimensional arrays A and S and to extract from said arrays A and S at least one of said first time distribution and said second time distribution.

20. A device for identifying at least one area in a surrounding diffusing medium, said at least one area having at least one absorption and/or diffusing coefficient different from that of said surrounding diffusing medium comprising:
   a) a pulse radiation source generating an excitation beam of said medium and of at least one of said area;
   b) a detector performing at least one acquisition of optical signal data, each acquisition including a first time distribution of a component of the optical signal due to at least one of said area, and a second time distribution of a spurious component due to a part of the medium other than said at least one area; and
   c) at least one processor configured to form a multidimensional array X from said optical signal data, to process said array X into a product of only two non-negative multidimensional arrays A and S and to extract from said arrays A and S at least one of said first time distribution and said second time distribution.

* * * * *